United States Patent [19]

Mericle

[11] 4,361,229
[45] Nov. 30, 1982

[54] CARTRIDGE FOR HEMOSTATIC CLIPS

[75] Inventor: Robert W. Mericle, Lebanon, N.J.

[73] Assignee: Ethicon, Inc., Somerville, N.J.

[21] Appl. No.: 289,430

[22] Filed: Aug. 3, 1981

[51] Int. Cl.³ .............................................. B65D 85/24
[52] U.S. Cl. ................................... 206/339; 206/341; 206/804; 128/325
[58] Field of Search ............... 206/339, 440, 804, 228, 206/229, 334, 336, 337, 341, 348, 355; 128/325

[56] References Cited

U.S. PATENT DOCUMENTS

| | | | |
|---|---|---|---|
| 3,713,533 | 1/1973 | Reimels | 206/339 |
| 4,146,130 | 3/1979 | Samuels et al. | 206/340 |
| 4,294,355 | 10/1981 | Jewusiak et al. | 206/339 |

*Primary Examiner*—Joseph Man-Fu Moy

[57] ABSTRACT

Cartridge containing a plurality of non-metallic, biocompatible hemostatic clips.

8 Claims, 7 Drawing Figures

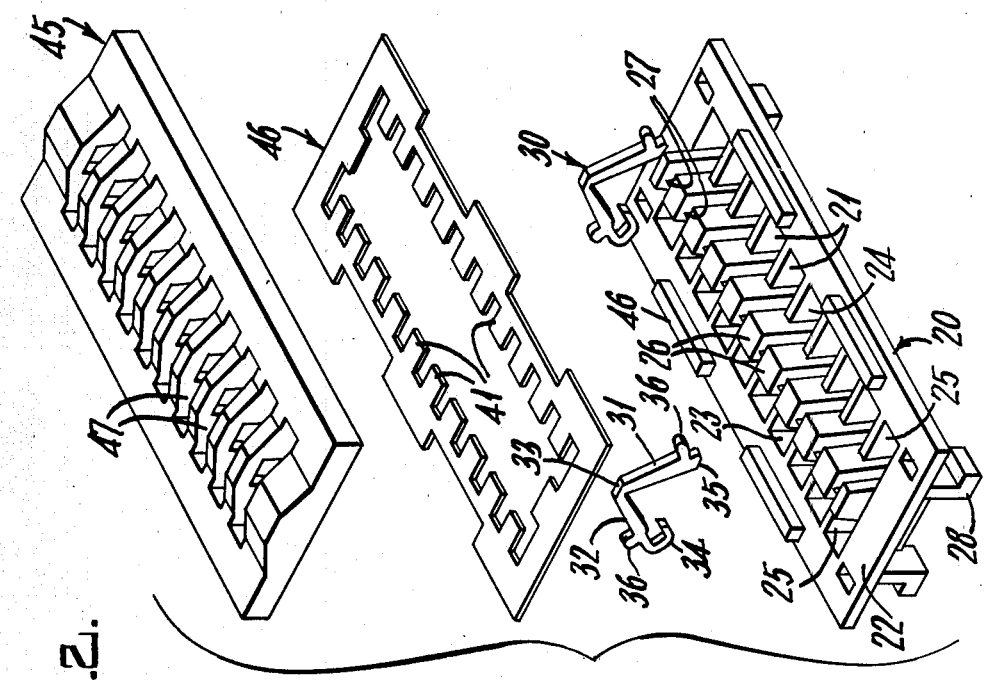
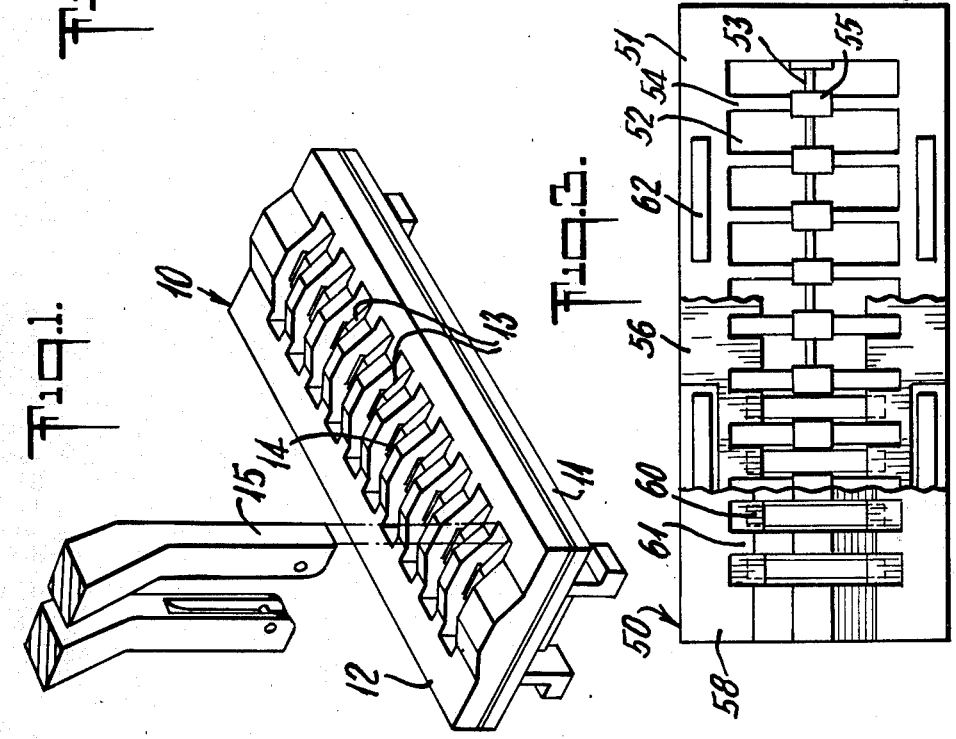

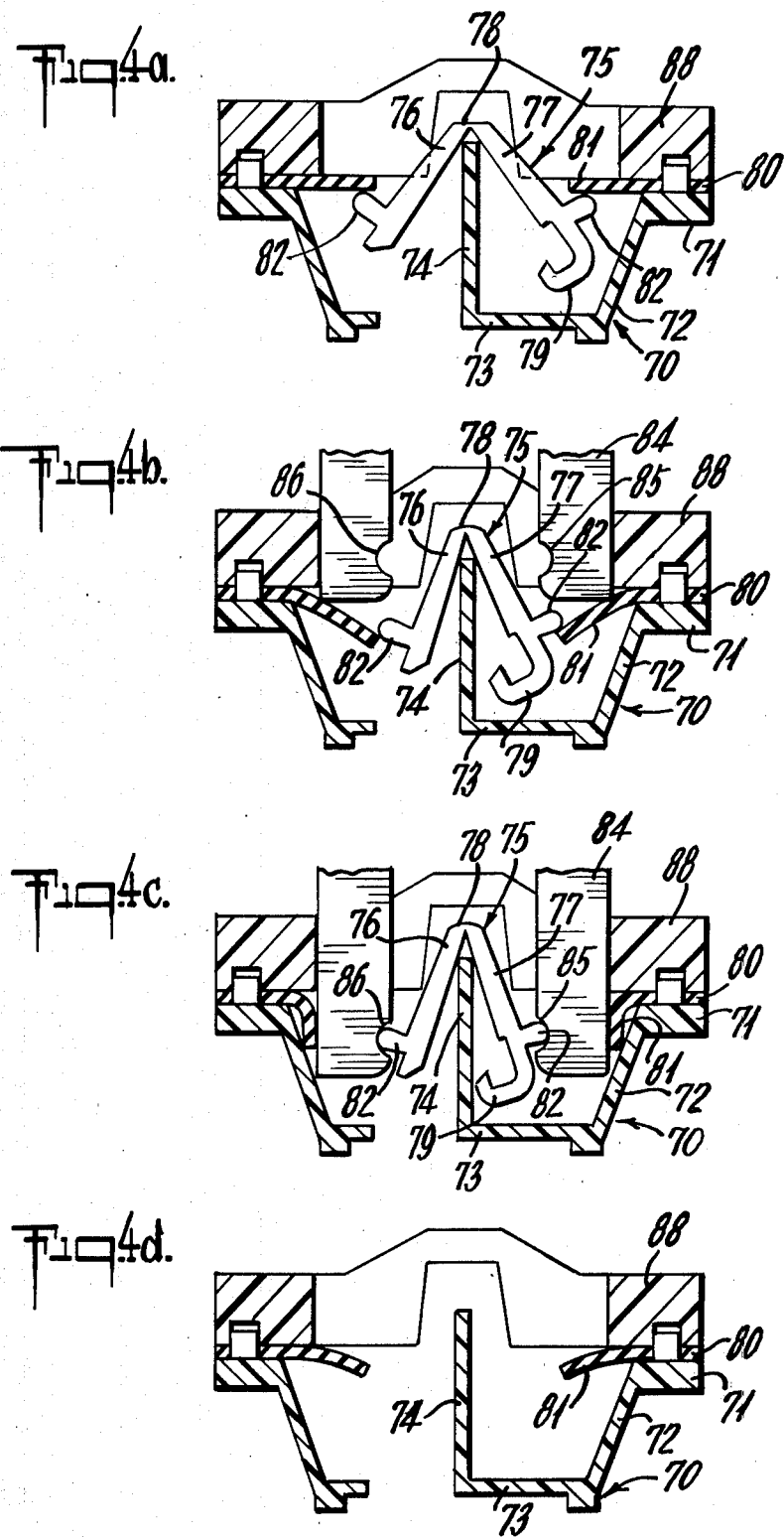

CARTRIDGE FOR HEMOSTATIC CLIPS

This invention relates to a cartridge containing a plurality of hemostatic clips and more particularly to a cartridge for non-metallic, bio-compatible hemostatic clips having a pair of leg members connected by a resilient hinge area.

BACKGROUND OF THE INVENTION

Conventional hemostatic clips of the prior art have been fabricated of stainless steel or tantalum, and are generally made from rectangular wires and formed into symmetrical V or U-shapes. Cartridges for such clips are typically comprised of open box-like structures sized to accept the appropriate U or V-shape with a center rail to support the clips in an inverted position. Various means have been provided to hold the clips on the rail until they are loaded into a forceps type applier. Typical of such prior art clips and cartridges are those illustrated in U.S. Pat. Nos. 3,713,533, 4,076,120, and 4,146,130.

Recent work in the field of molded hemostatic clips made from polymer materials; that is, bio-compatible and/or non-metallic materials, has resulted in a particularly useful clip design. The clip has a configuration wherein the legs are connected at their proximal ends by a resilient hinge area and the distal ends include appropriate latch means. The clip is formed in the open position and has means on the outer surface of its legs by which it can be picked up by a forceps-type applier. The forceps type applier may pick up the clip and the clip closed about a vessel by urging the legs of the clip towards one another until the latching means engages.

In certain of the prior art cartridges used with metal clips, the clip was held in the cartridge by placing the clip under stress so that it is lodged or wedged into a compartment. The stress is increased slightly in order to remove the clip from the cartridge. When making clips of the various polymer materials, it is desired that minimal or no stress be placed on the polymer for extended periods of time. This is especially true of the resilient hinge areas of the polymer clips which, if stressed for considerable lengths of time, that is, a year or more, could become brittle and not function as desired.

Hence, it is desired to produce a cartridge which will keep the non-metallic, bio-compatible clips in place without placing undue stress on the clips yet insure that the clips do not move from their initial position in the cartridge. It is desired that the cartridge be such that the clips may be placed in the cartridge and the cartridge sterilized and further handled with the clips remaining in the position in the cartridge where they were placed until easily removed by a simple forceps-type applying instrument. It is also important that on removing the clip from the cartridge no damage be done to the clip. The removal should be a simple and easy step for the nurse or surgeon using an appropriate forceps-type instrument.

SUMMARY OF THE PRESENT INVENTION

The present invention provides an improved cartridge for holding a plurality of non-metallic, bio-compatible hemostatic clips. Each clip comprises a pair of leg members connected at their proximal ends by a resilient hinge section and having latching means at their distal ends. My new cartridge holds the clips in spaced apart relationship in a manner so the cartridge may be readily sterilized and handled during surgical procedures without having the clips displaced from their position within the cartridge until it is desired to remove the clip. My new cartridge allows forceps-type applying instruments to be inserted into the cartridge and the clip removed with substantial ease from the cartridge.

In accordance with the present invention, the cartridge for holding the plurality of clips comprises a base member. The base member is divided into a plurality of compartments. Each of the compartments includes a recessed ledge dividing the compartment into two sections. The hinge of the clip is adapted to be placed on the ledge with the legs of the clip extending into opposite sections of a compartment on opposite sides of said ledge. The cartridge includes deflectable holding means which engage the outer leg surfaces of the clip. The cartridge also includes a cover member disposed on the base member and exposing the hinge portion of each clip in separate compartments. In use, the jaws of a forceps-type applying instrument are inserted through an opening in the cover member into a compartment. The jaws deflect the deflectable holding means and, in certain instances, may even close the clip slightly until the jaws engage the gripper applying means on the outer surface of the leg members of the clip. The jaws are removed from the compartment with the slightly closed clip in place in the jaws of the forceps-type applying instrument.

In a preferred embodiment of the present invention, the gripper applying means on the outer surface of the leg member is a cylindrical boss and the deflectable holding means within the cartridge is a patterned piece of paper. The paper is patterned to have a plurality of fingers with each finger engaging the top surface of a boss on each clip; i.e., the surface of the boss closest to the hinge area. In use, as the jaws of the forceps type applier are inserted into the compartment, the paper finger is deflected over the boss and a recess in the jaws allowed to engage the boss and the clip removed from the holder.

The invention will be more fully described in conjunction with the accompanying drawings.

DESCRIPTION OF THE DRAWINGS

FIG. 1 is a perspective view of a cartridge of the present invention including the jaws of a forceps-type gripper applying means schematically positioned above the compartment in the cartridge;

FIG. 2 is an exploded enlarged perspective view showing the various parts of the cartridge of the present invention;

FIG. 3 is an enlarged top view of the cartridge of the present invention with portions broken away to more clearly show the various parts of the cartridge;

FIG. 4a is a cross-sectional view of the cartridge of the present invention showing the clip in place;

FIG. 4b is a cross-sectional view of the cartridge of the present invention depicting an instrument being inserted for removal of a clip from the cartridge;

FIG. 4c is a cross-sectional view of the cartridge of the present invention with the jaws of the clip applying instrument in place ready to remove the clip from the cartridge;

FIG. 4d is a cross-sectional view of the cartridge of the present invention after the clip has been removed.

DETAILED DESCRIPTION OF THE EMBODIMENTS OF THE PRESENT INVENTION

Referring to the drawings, in FIG. 1 there is shown a cartridge 10 of the present invention comprising a base member 11 and a cover member 12 which form a plurality of compartments 13. A clip 14 is disposed in each of the compartments. The figure also shows the jaws 15 of a forceps type applying instrument positioned directly above one of the compartments and in position to be brought vertically down into the compartment for removal of a clip.

In FIG. 2, the cartridge of FIG. 1 has been exploded in a perspective view to show the various parts of the cartridge. The base member 20 comprises a plurality of compartments 21. The compartments are surrounded about the entire periphery of the cartridge by a ledge 22. Each compartment comprises two sections 23 and 24. The compartments are separated from adjacent compartments by lateral members 25 extending from the top of the ledge to the floor of the compartment and by central members 26 between the lateral members which extend from above the lateral members to the floor of the compartment. Each compartment is separated into two sections 23 and 24 and these sections are separated by a recessed ledge 27 extending from just below the central member separating compartments to the floor of the compartments.

Projections or legs 28 extend from the base member. These legs are configured so as to mate with a weighted base or stand to improve the stability of the cartridge and facilitate clip removal.

A clip comprises a pair of leg members 31 and 32 connected at their proximal ends by a hinge area 33 and terminating at their distal ends in a latch means 34 and 35. In this embodiment, the latch means of the clip is a deflectable hook member 34 at the distal end of one of the leg members which is deflected by the distal end 35 of the other leg member upon the closing of the clip. On the outer surface of each leg member, there is a suitable gripper applying means for picking up the clip by the appropriate forceps-type instrument. In this embodiment, the means comprises a cylindrical boss 36 disposed on the outer surface of the clip.

Each compartment 21 contains a clip 30 with the clip sitting in the compartment with its hinge area positioned on top of the recessed ledge 27 separating the two sections of the compartment and with a leg member of each clip extending into opposed open sections 23 and 24 of each compartment. Extending about the outer ledge of the base member is a deflectable holding means 40. In this embodiment, the holding means is made of paper, though any resilient, readily bendable material may be used. The holding means sits on the ledge 22 of the base member and has a plurality of fingers 41. A finger extends into each section of a compartment to the point where it just engages the gripper applying means 36 on the clip. This will be better seen in the cross-sectional views shown in FIGS. 4a through d.

A cover member 45 is either welded or pressed on top of the base member. In this instance, a plurality of lugs 46 on the base member are pressed in suitable recesses in the cover member. The cover member has a peripheral portion sitting about the ledge of the base member and has a plurality of transverse members 47 which extend across the cover member and are positioned to separate each of the compartments.

Referring to FIG. 3, there is shown a top view of a cartridge of the present invention with portions broken away for the sake of clarity. The cartridge 50 comprises a base member 51 having a plurality of compartments 52. The compartments are separated into two adjacent sections by a member 53 on which the hinge area of a clip 60 rests. Adjacent compartments are separated by lateral walls 54 and a central wider wall 55. The center wider wall is sufficiently wide so it just engages the sides of a clip as the clip sits on member 53. The wider central wall prevents relative lateral movement of the clip in the compartment and provides for locating each clip centrally in a compartment. This later function assists in removing clips from the cartridge with a suitable applier in that it prevents each clip in a uniform manner to the applier. The base member has a ledge about its entire periphery. Positioned on this ledge is a deflectable holding means 56. The deflectable holding means includes fingers which extend into the sections of each compartment. The fingers of the deflectable holding means extend sufficiently far into the compartment to engage the outer surfaces of the clips and restrain movement of the clips as will be more fully explained in conjunction with FIGS. 4a–d. A cover member 58 extends around the entire periphery of the base member. The cover member has transversely extending members 61 which separate the compartments. Raised areas 62 positioned on the periphery of the base member fit into recessed areas in the cover member to maintain the parts of the cartridge in their appropriate positions.

In FIGS. 4a through 4d, like numerals are used for like parts in each of the Figures. The four figures are cross-sectional views of the cartridge of the present invention in various stages of clip removal. Referring to FIGS. 4a–d, the base member 70 comprises an outer ledge 71 extending from the side walls 72 of the base member. The base member includes a bottom 73 and a central vertical wall 74. A clip 75 comprising a pair of leg members 76 and 77 connected at their proximal ends by a hinge 78 sits on the vertical wall with the hinge on the wall and the leg members extending into compartments in the base member. The distal ends of the leg members terminate in latch means and in this embodiment one of the distal legs comprises a hook member 79 which is adapted to be deflected and close about the distal end of the opposite leg member. Placed in position about the ledge 71 is a suitable deflectable paper 80 with fingers 81 of the paper extending inwardly towards the clip and just engage the outer surfaces of the clip. In the embodiment shown, the clip has a pair of cylindrical bosses 82 on the leg members. The bosses are gripped by a suitable forceps-type gripper applying instrument in order to remove the clip from the cartridge and place the clip where desired. As more clearly seen in FIG. 4b, the instrument 24 has a pair of recesses 85 and 86 which will engage the cylindrical bosses of the clip. A cover member 88 is pressed or welded to the lateral edge of the base member and secures the deflectable means in place.

As more clearly seen in FIG. 4b, as the jaws of the forceps-type gripper applying instrument are inserted into a compartment, they first deflect the fingers of the paper. As the instrument is further inserted into the compartment as seen in FIG. 4c, the jaws further deflect the paper finger, and the recesses of the jaws engage the cylindrical bosses of the clip slightly compressing or slightly closing the clip. The instrument is removed and as shown in FIG. 4d, an empty compartment is depicted.

It is preferred that the deflectable paper finger be slightly wider than the width of the opening in the cover member to prevent deflection upward and premature removal of the clip should the cartridge be dropped or turned over or the like. The wider finger also bears against the bottom of the cover member to apply a small preload to the clip which aids in balancing the clip on the ledge and prevents rattling of the clip or movement of the clips in the cartridge.

The cartridges of the present invention are conveniently molded of various plastic materials and are discarded after the clips have been removed. After loading the clips in the cartridge, the deflectable means is inserted and the cover plate or cover member welded or pressed onto the base member in accordance with conventional plastic techniques. The entire unit is sterilized with, for example, ethylene oxide, and packaged in a sterile enclosure until ready for use. In the event the clips are formed of a moisture sensitive absorbent material, such as a polydioxanone, the assembly unit is dessicated and placed in a dry sealed package to prevent degradation of the clips during storage. When the clips are fabricated of a non-absorbable material such as nylon or polypropylene, the requirement to exclude all traces of moisture from the package is not necessary.

While the foregoing has described the embodiments of the cartridge of the present invention, other embodiments will readily be apparent to those skilled in the art.

I claim:

1. A cartridge for holding a plurality of bio-compatible, non-metallic hemostatic clips, each of said clips having a pair of leg members connected at their proximal ends by a resilient hinge, said clips having removing means on the outer surfaces of said leg members by which the clips may be removed from said cartridge by a forceps-type applying instrument, said cartridge comprising:
   (a) a base member, said base member being divided into a plurality of compartments, each of said compartments including a recessed ledge on which the hinge of the clip is adapted to be placed, with the legs extending into the compartment on opposite sides of said ledge;
   (b) a deflectable holding means comprising a patterned piece of paper and engaging the clip removing means on both legs of said clip, and
   (c) a cover member disposed on top of the base member and exposing the clips in separate compartments whereby the jaws of a forceps type applying instrument may be inserted through an opening in the cover member into a compartment to deflect the holding means and engage the removing means on the outer surface of the leg member of said clip and remove said clip from said cartridge.

2. A cartridge according to claim 1 wherein said paper having deflectable fingers extending into each compartment and engaging the removing means on the legs of the clip.

3. A cartridge according to claim 1 or 2 wherein the removing means on the outer surfaces of said leg members of the clips are cylindrical bosses.

4. A cartridge according to claim 2 or 3 wherein the deflectable fingers are slightly wider than the openings in the cover member to aid in stabilizing the clips in the cartridge.

5. A cartridge for holding a plurality of bio-compatible, non-metallic clips, each of said clips comprising two legs joined by an integral hinge, one of said legs terminating at its distal end in a hook member adapted to receive and hold the distal end of the other leg when said clip is closed, and said legs carrying on their outer surface means by which the may be gripped by a forceps type applying instrument and removed from the cartridge said cartridge comprising:
   (a) a base member, said base member comprising a pair of longitudinally extending side walls and a pair of end walls forming a substantially rectangular opening in said base member, a ledge extending outwardly from said opening about the entire periphery thereof, said rectangular opening being separated into a plurality of compartments by vertical members extending transverse of said base member, each compartment being substantially rectangular in shape with the longer sides of the rectangle extending the width of the base member, each compartment being separated into two sections by a vertical member extending longitudinally of said base member, the said longitudinally extending member extending above the rectangular opening;
   (b) a plurality of clips positioned in said base member with a single clip positioned in each compartment, the hinge of said clip resting on the longitudinally extending member with the legs of the clip extending downwardly into opposite sections of the compartment;
   (c) widened portions extending between the central part of each compartment for engaging the side surfaces of the clips at the hinge area thereof to prevent lateral movement of the clips and locate the clips centrally of the compartment to aid in the applier pick-up;
   (d) a deflectable holding member comprising a patterned piece of paper, said holding member extending about the periphery of the base member and having fingers extending into sections of compartments to engage the outer surface of the leg of the clip sitting in said compartment; whereby deflection of the clip is prevented, and
   (e) a cover member disposed on top of said deflectable holding member and extending about the entire periphery of said base member and having a plurality of compartments in line with the compartments in the base member whereby a plurality of openings are formed in said cartridge exposing the hinge portion of the clip and a portion of the legs of each clip for easy accessibility to the clips.

6. A cartridge according to claim 5 wherein the two sections of each compartment are substantially identical.

7. A cartridge according to claim 5 wherein the cover member is secured to the base member by press fitting the two members together.

8. A cartridge according to claim 5 wherein the fingers of the deflectable holding means are wider than the openings in the cover member to aid in stabilizing the clips in the cartridge.

* * * * *